United States Patent
Hugg et al.

(10) Patent No.: US 7,470,907 B2
(45) Date of Patent: Dec. 30, 2008

(54) CROSS-SLIT COLLIMATOR METHOD AND SYSTEM

(75) Inventors: James William Hugg, Glenville, NY (US); Jorge Uribe, Niskayuna, NY (US); Floribertus P. M. Heukensfeldt Jansen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/639,786

(22) Filed: Dec. 15, 2006

(65) Prior Publication Data

US 2008/0142719 A1 Jun. 19, 2008

(51) Int. Cl.
*G01T 1/20* (2006.01)
(52) U.S. Cl. .................................. 250/363.1
(58) Field of Classification Search .. 250/363.01–363.1
See application file for complete search history.

(56) References Cited

U.S. PATENT DOCUMENTS

| | | | |
|---|---|---|---|
| 4,289,965 A | | 9/1981 | Koga |
| 4,389,569 A | * | 6/1983 | Hattori et al. .......... 250/363.04 |
| 4,748,328 A | * | 5/1988 | Chang et al. ........... 250/363.04 |
| 5,021,667 A | * | 6/1991 | Genna et al. ............. 250/363.1 |
| 5,032,728 A | * | 7/1991 | Chang et al. ........... 250/363.04 |
| 5,059,799 A | * | 10/1991 | Kurakake ................ 250/363.1 |
| 5,591,976 A | * | 1/1997 | Berthold et al. .......... 250/363.1 |
| 5,991,356 A | * | 11/1999 | Horiuchi et al. ................ 378/8 |
| 6,504,157 B2 | | 1/2003 | Juhi |
| 6,525,320 B1 | | 2/2003 | Juni |
| 6,525,321 B2 | | 2/2003 | Juni |
| D474,277 S | | 5/2003 | Juni |
| D492,998 S | | 7/2004 | Juni |
| 7,012,257 B2 | | 3/2006 | Juni |
| 7,015,476 B2 | | 3/2006 | Juni |

(Continued)

FOREIGN PATENT DOCUMENTS

WO    WO 00/62093    10/2000

(Continued)

OTHER PUBLICATIONS

De Kuhl and RQ Edwards, Cylindrical and Section Radioisotope Scanning of the Liver and Brain, Radiology, 1964, vol. 83, pp. 926-935.

(Continued)

*Primary Examiner*—David P Porta
*Assistant Examiner*—Kiho Kim
(74) *Attorney, Agent, or Firm*—Fletcher Yoder

(57) ABSTRACT

Collimator assemblies that include an outer slit collimator having one or more slits therein, and an inner slit collimator having one or more slits therein are provided. Imaging systems that include a collimator assembly and a detector array are also provided. The collimator assembly includes an outer slit collimator having one or more slits therein. The collimator assembly further includes an inner slit collimator having one or more slits therein. The imaging system also includes a detector array configured to detect gamma rays emanating from a field of view that pass through one or more apertures defined by the collimator assembly. The detector array is further configured to generate one or more signals in response to the detected gamma rays. Methods of imaging a field of view using the imaging system are also provided.

28 Claims, 5 Drawing Sheets

U.S. PATENT DOCUMENTS

| | | | |
|---|---|---|---|
| 7,071,473 | B2 | 7/2006 | Juni |
| 7,105,825 | B2 | 9/2006 | Juni |
| 7,138,638 | B2 | 11/2006 | Juni |
| 2002/0003859 | A1* | 1/2002 | Kogan .......................... 378/84 |
| 2004/0239941 | A1 | 12/2004 | Schramm |
| 2005/0243422 | A1* | 11/2005 | Distler et al. ............... 359/566 |
| 2006/0050845 | A1 | 3/2006 | Juni |
| 2006/0182223 | A1* | 8/2006 | Heuscher .................... 378/137 |
| 2006/0192308 | A1 | 8/2006 | Juni |
| 2006/0233298 | A1* | 10/2006 | Igarashi et al. ................ 378/19 |
| 2007/0007455 | A1 | 1/2007 | Juni |

FOREIGN PATENT DOCUMENTS

| | | |
|---|---|---|
| WO | WO 2004/072679 | 8/2004 |
| WO | WO 2005/006977 | 1/2005 |
| WO | WO 2005/052634 | 6/2005 |
| WO | WO 2006/029163 | 3/2006 |
| WO | WO 2006/050845 | 3/2006 |
| WO | WO 2006/065441 | 6/2006 |

OTHER PUBLICATIONS

De Kuhl, RQ Edwards and AR Ricci, The Mark III Scanner: A Compact Device for Multiple-View and Section Scanning of the Brain, Radiology, 1970, vol. 96, pp. 563-570.

De Kuhl, RQ Edwards, AR Ricci, RJ Yacob, TJ Mich and A Alavi, The Mark IV System for Radionuclide Computed Tomography of the Brain, Radiology, 1976, vol. 121, pp. 405-413.

GF Knoll and JJ Williams, Application of a Ring Pseudorandom Aperture for Transverse Section Tomography, IEEE Transactions on Nuclear Science, 1977, vol. NS-24, pp. 581-586.

JJ Williams, WP Snapp and GF Knoll, Introducing Sprint: A single Photon Ring System for Emission Tomography, IEEE Transactions on Nuclear Science, 1979, vol. NS-26, pp. 628-633.

M Tanaka, Y Hirose, K Koga and H Hattori, Engineering Aspects of a Hybrid Emission Computed Tomograph, IEEE Transactions on Nuclear Science, 1981, vol. NS-28, pp. 137-141.

WL Rogers, NH Clinthorne, J Stamos, KF Koral, R Mayans, JW Keyes, Jr., JJ Williams, WP Snapp and GF Knoll, Sprint: A Stationary Detector Single Photon Ring Tomograph for Brain Imaging, IEEE Transactions on Medical Imaging, 1982, vol. MI-1, pp. 63-68.

Y Hirose, Y Ikeda, Y Higashi, K Koga, H. Hattori, I Kanno, Y Miura, S Miura and K Uemura, A Hybrid Emission CT, IEEE Transactions on Nuclear Science, 1982, vol. NS-29, pp. 520,523.

Gf Knoll, Single-Photon Emission Computed Tomography, IEEE Proc., 1983, vol. 71, pp. 320-332.

WL Rogers, NH Clinthorne, J Stamos, KF Koral, R Mayans, GF Knoll J Juni, JW Keyes, Jr. and BA Harkness, Performance Evaluation of Sprint, A Single Photon Ring Tomograph for Brain Imaging, J. Nucl. Med., 1984, vol. 25, pp. 1013-1018.

WL Rogers, NH Clinthorne, L. Shao, P Chiao, Y Ding, JA Stamos and KF Koral, Sprint II: A Second Generation Single Photon Ring Tomograph, IEEE Transactions on Medical Imaging, 1988, vol. 7, pp. 291-297.

GL Zeng, Q Huang, Q Tang and WJ Wright, Skew-Slit Collimator for Small Animal SPECT, Society of Nuclear Medicine, Jun. 7, 2006, Oral Presentation, Abstract #664.

JW Hugg, E Asma, J Uribe, FP Jansen, RM Manjeshwar, H Lai, JC Paing, JR Dubois and X Guo, A Small-Animal SPECT/CT System for Dynamic Preclinical Imaging, Dynamic Nuclear Medicine Workshop: Oral Presentation, Abstract Banff International Research Station, Mar. 28, 2006.

JW Hugg, FP Jansen, J Uribe, RM Manjeshwar, H Lai, JC Pang and X Guo, A Small Animal SPECT/CT System with a Stationary CZT Detector Ring and Rotating Multiple Slit or Pinhole Collimator, Oral Presentation, Abstract M13-4, IEEE Medical Imaging Conference, San Diego, Nov. 4, 2006.

JW Hugg, FP Jansen, J Uribe, RM Manjeshwar, H. Lai, JC Pang and X Guo, Design of a Small-Animal SPECT System with a Stationary CZT Detector Ring, Oral Presentation, Abstract MR01-4, IEEE/Room Temperature Semiconductor Detector Conference, San Diego, Nov. 1, 2006.

JW Hugg, FP Jansen, J Uribe, and RM Manjeshwar, Design of Multi-Slit and Multi-Pinhole Collimators for a Small-Animal SPECT System with a Stationary CZT Detector Ring, Poster Abstract M06-26, IEEE Medical Imaging Conference, San Diego, Nov. 2, 2006.

J Hugg, J Uribe, F Jansen, R Manjeshwar, H Lai, J Pang, J Dubois and X Guo, Small-Animal SPECT/CT Pre-Clinical Imaging System, Poster Abstract 168, Academy of Molecular Imaging Orlando, Mar. 25, 2006.

JW Hugg, J Uribe, FP Jansen, RM Manjeshwar, H Lai, JC Pang, JR Dubois and X Guo, A Small-Animal MicroSPECT/MicroCT System with a Stationary CZT Detector Ring and Rotating Multi-Pinhole and Multi-Slit Collimators, Oral Presentation, Abstract 663, Society of Nuclear Medicine, San Diego, Jun. 7, 2006.

JW Hugg, FP Jansen, J Uribe, RM Manjeshwar, JC Pang, H Lai and X Guo, A Small-Animal SPECT/CT System with a Stationary CZT Detector Ring for Dynamic Preclinical Imaging, Poster Abstract 782, Society of Molecular Imaging, Honolulu, Sep. 2, 2006.

JW Hugg, J Uribe, FP Jansen, RM Manjeshwar, H Lai, JC Pang, JR Dubois and X Guo, A Small Animal SPECT/CT System with a Stationary CZT Detector Ring and Rotating Multi-Pinhole and Multi-Slit Collimators, Oral Presentation and Abstract, Workshop on Small-Animal SPECT, University of Arizona, Tucson, Mar. 9, 2006.

* cited by examiner

CROSS-SLIT COLLIMATOR METHOD AND SYSTEM

BACKGROUND

The invention relates generally to non-invasive imaging such as single photon emission computed tomography (SPECT) imaging. More particularly, the invention relates to cross-slit collimators for use in non-invasive imaging.

SPECT is used for a wide variety of imaging applications, such as medical imaging. In general, SPECT systems are imaging systems that are configured to generate an image based upon the impact of photons (generated by a nuclear decay event) against a gamma-ray detector. In medical and research contexts, these detected photons may be processed to formulate an image of organs or tissues beneath the skin.

To produce an image, one or more detector assemblies may be rotated around a subject. Detector assemblies are typically comprised of a plurality of structures working together to receive and process the incoming photons. For instance, the detector assembly may utilize a scintillator assembly (e.g., large sodium iodide scintillator plates) to convert the photons into light for detection by an optical sensor. This scintillator assembly may be coupled by a light guide to multiple photomultiplier tubes (PMTs) or other light sensors that convert the light from the scintillator assembly into an electric signal. In addition to the scintillator assembly-PMT combination, pixilated solid-state direct conversion detectors (e.g., CZT) may also be used to generate electric signals from the impact of the photons. This electric signal can be easily transferred, converted, and processed by electronic modules in a data acquisition module to facilitate viewing and manipulation by clinicians.

Typically, SPECT systems further include a collimator assembly that may be attached to the front of the gamma-ray detector. In general, the collimator assembly is designed to absorb photons such that only photons traveling in certain directions impact the detector assembly. For example, multihole collimators comprised of multiple, small-diameter channels separated by lead septa have been used. With these multihole collimators, photons that are not traveling through the channels in a direction generally parallel to the lead septa are absorbed. In addition, while parallel-hole collimators are typically used, collimators also may have converging holes for image magnification or diverging holes for minifying the image. For improved resolution, a pinhole collimator may be used. By way of example, an improved image resolution may be obtained with a pinhole collimator, e.g., if the subject is closer to the pinhole than the pinhole is to the gamma-ray detector.

While current SPECT systems have been used successfully, these systems have a number of disadvantages. For instance, rotation of the gamma-ray detectors along with the corresponding collimator assemblies around the subject typically requires large and expensive positioning systems capable of rotating the equipment with the needed precision. In addition, extended examination times are typically required because the detector assemblies must be rotated around the subject to obtain images from multiple angles around the subject. Moreover, current systems also do not provide the desired resolution and sensitivity. By way of example, the sensitivity of SPECT systems with multi-hole collimators may be reduced because only photons traveling in a direction generally parallel to the axis of the holes pass through the collimator. For similar reasons, SPECT systems with multi-hole collimators also may not provide the desired positional resolution.

Accordingly, it would be desirable to provide an imaging system with improved positional resolution and sensitivity while also having reduced examination times and simpler positioning systems.

BRIEF DESCRIPTION

In accordance with one embodiment, the present technique provides a collimator assembly. The collimator assembly includes an outer slit collimator having one or more slits therein. The collimator assembly further includes an inner slit collimator having one or more slits therein.

In accordance with another embodiment, the present technique provides an imaging system. The imaging system includes a collimator assembly and a detector array. The collimator assembly includes an outer slit collimator having one or more slits therein. The collimator assembly further includes an inner slit collimator having one or more slits therein. The imaging system also includes a detector array configured to detect gamma rays emanating from a field of view that pass through one or more apertures defined by the collimator assembly. The detector array is further configured to generate one or more signals in response to the detected gamma rays.

In accordance with yet another embodiment, the present technique provides a method of imaging a volume. The method includes positioning at least a portion of a subject in a field of view of a SPECT system. The method further includes collimating gamma rays emitted from the portion of the subject using a collimator assembly that comprises an outer slit collimator and an inner slit collimator. Gamma rays aligned with apertures formed by overlapping slits of the outer slit collimator and the inner slit collimator pass through the collimator assembly. The collimator assembly absorbs gamma rays not aligned with the apertures. The method further includes detecting gamma rays that pass through the collimator assembly. The method further includes generating one or more signals in response to the detected gamma rays.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
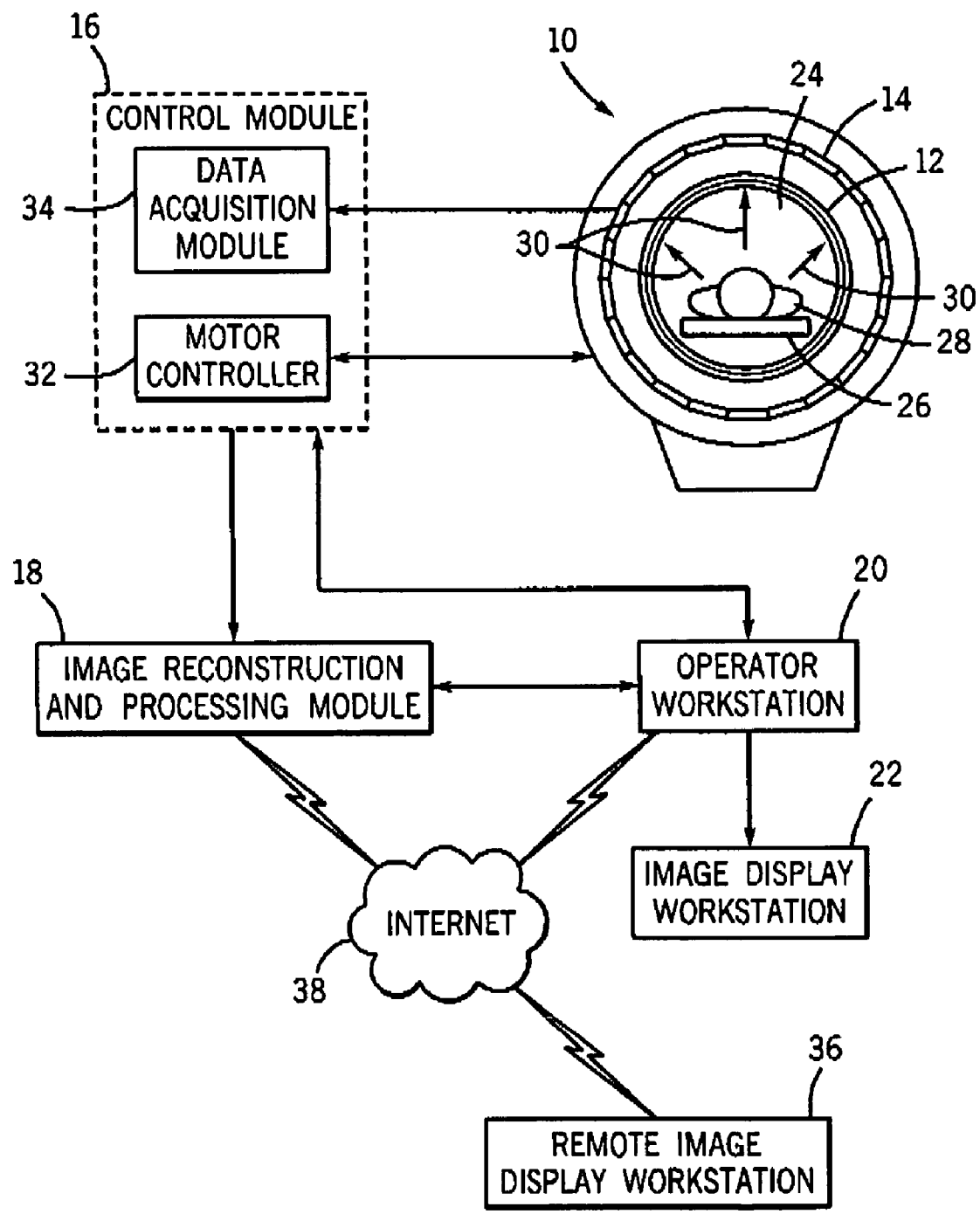
FIG. 1 is an illustration of an exemplary SPECT system which may include a collimator assembly in accordance with embodiments of the present technique.

FIG. 1 illustrates an exemplary SPECT system 10 for acquiring and processing image data in accordance with exemplary embodiments of the present technique. In the illustrated embodiment, SPECT system 10 includes a collimator assembly 12 and a detector array 14. The SPECT system 10 also includes a control module 16, an image reconstruction and processing module 18, an operator workstation 20, and an image display workstation 22. Each of the aforementioned components will be discussed in greater detail in the sections that follow.

SPECT system 10 also includes a field of view 24 into which a subject support 26 (e.g. a table) may be positioned for supporting the subject 28 (e.g., a human patient, a small animal, a plant, a porous object, etc.) in a generally stationary position in the field of view 24 for scanning. Alternatively, the subject support 26 may be stationary, while the SPECT system 10 may be positioned around the subject 28 for imaging. Those of ordinary skill in the art will appreciate that the subject 28 may be positioned in any suitable position, for example, generally vertical, generally horizontal, or any other suitable position for the desired scan. In SPECT imaging, the subject 28 is typically injected with a solution that contains a radioactive tracer. The solution is distributed and absorbed throughout the subject in different degrees, depending on the tracer employed and, in the case of living subjects, the functioning of the organs and tissues. The radioactive tracer emits electromagnetic rays (e.g., photons or gamma quanta) known as "gamma rays" during a nuclear decay event.

As previously mentioned, the SPECT system 10 includes the collimator assembly 12 that receives the gamma rays 30 emanating from the field of view 24. As will be described below, the collimator assembly 12 is generally configured to limit and define the direction and angular divergence of the gamma rays 30. In general, the collimator assembly 12 is disposed between the detector array 14 and the field of view 24. In accordance with exemplary embodiments of the present technique, the collimator assembly 12 includes an outer slit collimator and an inner slit collimator disposed closer to the imaging volume than the outer slit collimator. In general, the inner and outer slit collimators may contain a radiation absorbent material, such as lead or tungsten, for example. As will be discussed in more detail below, the inner and outer slit collimators each contain one or more slits that define one or more apertures through the collimator assembly 12. In the illustrated embodiment, the collimator assembly 12 extends at least partially around the field of view 24. In exemplary embodiments, the collimator assembly 12 may extend up to about 360° around the field of view 24. By way of example, the collimator assembly 12 may extend from about 180° to about 360° around the field of view 24.

The gamma rays 30 that pass through the collimator assembly 12 impact the detector array 14. Due to the collimation of the gamma rays 30 by the collimator assembly 12, the detection of the gamma rays 30 may be used to determine the line of response along which each of the gamma rays 30 traveled before impacting the detector array 14, allowing localization of each gamma ray's origin to that line. In general, the detector array 14 includes a plurality of detector elements configured to detect the gamma rays 30 emanating from the field of view 24 and passing through one or more apertures defined by the collimator assembly 12. In exemplary embodiments, each of the plurality of detector elements in the detector array 14 produces an electrical signal in response to the impact of the gamma rays 30.

As will be appreciated by those of ordinary skill in the art, the detector elements of the detector array 14 may include any of a variety of suitable materials and/or circuits for detecting the impact of the gamma rays 30. By way of example, the detector elements may include a plurality of solid-state detector elements, which may be provided as one-dimensional or two-dimensional arrays. In another embodiment, the detector elements of the detector array 30 may include a scintillation assembly and PMTs or other light sensors.

Moreover, the detector elements may be arranged in the detector array 14 in any suitable manner. By way of example, the detector array 14 should generally extend at least partially around the field of view 24. In certain embodiments, the detector array may include modular detector elements arranged around the field of view 24. Alternatively, the detector array 14 may be arranged in a ring that may extend up to about 360° around the field of view 24. In certain exemplary embodiments, the detector array 14 may extend from about 180° to about 360° around the field of view 24. The ring of detector elements may include flat panels or curved detector surfaces (e.g., a NaI annulus). In one exemplary embodiment, the ring may comprise in the range from 9-10 solid-state detector panels with each detector panel comprising four detector modules. Those of ordinary skill in the art will appreciate that the ring need not be circular, for example, the detector elements may be arranged in an elliptical ring or be contoured to the body profile of the subject 28. In addition, in certain exemplary embodiments, the detector array 14 may be gimbaled on its support base, e.g., so that arbitrary slice angles may be acquired.

To acquire multiple lines of response emanating from the field of view 24 during a scan, the collimator assembly 12 may be configured to rotate about the subject 28 positioned within the field of view 24. In certain exemplary embodiments, the collimator assembly 12 may be configured to rotate with respect to the detector array 14. By way of example, the detector array 14 may be stationary while the collimator assembly 12 may be configured to rotate about the field of view 24. In certain exemplary embodiments, the collimator assembly 12 and the detector array 14 may both be configured to rotate, either together or independently.

SPECT system 10 further includes a control module 16. In the illustrated embodiment, the control module 16 includes a motor controller 32 and a data acquisition module 34. In general, the motor controller 32 may control the rotational speed and position of the collimator assembly 12, the detector array 14, and/or the position of the subject support 26. The data acquisition module 34 is configured to obtain the signals generated in response to the impact of the gamma rays 30 with the detector array 14. For example, the data acquisition module 34 may receive sampled analog signals from the detector assembly 14 and convert the data to digital signals for subsequent processing by an image reconstruction and processing module 18.

Those of ordinary skill in the art will appreciate that any suitable technique for data acquisition may be used with SPECT system 10. By way of example, the data needed for image reconstruction may be acquired in a list or a frame mode.

In one exemplary embodiment of the present technique, gamma ray events (e.g., the impact of gamma rays 30 on the detector array 14), gantry motion (e.g., collimator assembly 12 motion and subject support 26 position), and physiological signals (e.g., heart beat and respiration) may be acquired in a list mode. For example, a time-stamp may be associated with each gamma ray event (e.g., energy and position) or by interspersing regular time stamps (e.g., every 1 ms) into the list of gamma ray events. The physiological signals may be included in the list, for example, when they change by a defined amount or with every regular time stamp. In addition, gantry motion may also be included in the event lists, for example, when they change by a defined amount or with every regular time stamp. The list mode data may be binned by time, gantry motion or physiological gates before reconstruction. List mode may be suitable in exemplary embodiments where the count rate is relatively low and many pixels record no counts at each gantry position or physiological gate.

Alternatively, frames and physiological gates may be acquired by moving the gantry in a step-and-shoot manner and storing the number of events in each pixel during each frame time and heart or respiration cycle phase. Frame mode may be suitable, for example, where the count rate is relatively high and most pixels are recording counts at each gantry position or physiological gate.

The image reconstruction and processing module 18 is coupled to the data acquisition module 34. The signals acquired by the data acquisition module 34 are provided to the image reconstruction and processing module 18 for image reconstruction. The reconstructed image may be provided to the operator workstation 20. The operator workstation 20 may be utilized by a system operator to provide control instructions to some or all of the described components and for configuring the various operating parameters that aid in data acquisition and image generation. An image display workstation 22 coupled to the operator workstation 20 may be utilized to observe the reconstructed image. It should be further noted that the operator workstation 20 and the image display workstation 22 may be coupled to other output devices, which may include printers and standard or special purpose computer monitors. In general, displays, printers, workstations, and similar devices supplied with the SPECT system 10 may be local to the data acquisition components, or may be remote from these components, such as elsewhere within the institution or hospital, or in an entirely different location, linked to the image acquisition system via one or more configurable networks, such as the Internet, virtual private networks, and so forth. By way of example, the operator workstation 20 and/or the image reconstruction and processing module 18 may be coupled to a remote image display workstation 36 via a network (represented on FIG. 1 as Internet 38).

Furthermore, those of ordinary skill in the art will appreciate that any suitable technique for image reconstruction may be used with the SPECT system 10. In one exemplary embodiment, iterative reconstruction (e.g., ordered subsets expectation maximization, OSEM) may be used. Iterative reconstruction may be suitable for certain implementations of the SPECT system 10 due, for example, to its speed and the ability to tradeoff reconstruction resolution and noise by varying the convergence and number of iterations.

While in the illustrated embodiment, the control module 16 (including the data acquisition module 34 and the motor controller 32) and the image reconstruction and processing module 18 are shown as being outside the detector array 14 and the operator workstation 20. In certain other implementations, some or all of these components may be provided as part of the detector array 14, the operator workstation 20, and/or other components of the SPECT system 10.

Figure 2:
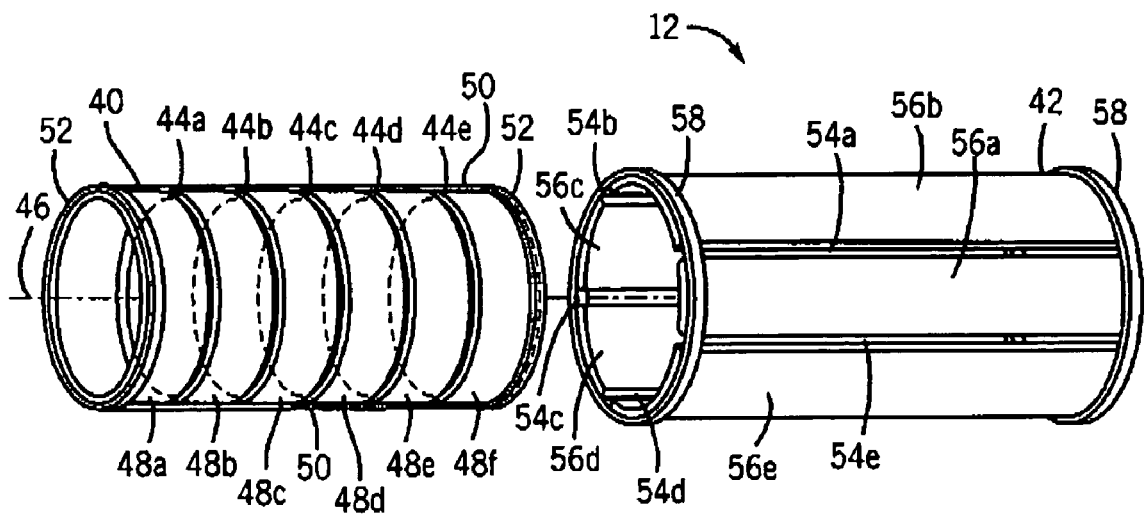
FIG. 2 is an illustration of an arrangement of an exemplary collimator assembly comprising an inner slit collimator and an outer slit collimator, in accordance with embodiments of the present technique.

Referring now to FIG. 2, an exploded view of the collimator assembly 12, is illustrated, which may be configured in accordance with exemplary embodiments of the present technique. As previously described with respect to FIG. 1, the collimator assembly 12 includes an inner slit collimator 40 proximate to a volume (e.g., the field of view 24 illustrated on FIG. 1) and an outer slit collimator 42. As illustrated, the collimator assembly 12 at least partially encloses the field of view 24. While FIG. 2 is an exploded view, the collimator assembly 12 should be assembled so that the inner slit collimator 40 is disposed closer to the field of view 24 than the outer slit collimator 42. As will be discussed in more detail below, the collimator assembly 12 should be configured such that the inner slits 44*a*-44*e* in the inner slit collimator 40 and the outer slits 54*a*-54*e* in the outer slit collimator 42 define one or more apertures through the collimator assembly 12. Moreover, spacing between the inner surface(s) of the outer slit collimator 42 and the outer surface(s) of the inner slit collimator 40 may be chosen to position the outer slit collimator 42 anywhere in the volume between the inner slit collimator 40 and the detector assembly 14. By way of example, the outer slit collimator 42 may be positioned close to but not touching the inner slit collimator 40.

While the inner slit collimator 40 and the outer slit collimator 42 are illustrated as being generally cylindrically shaped, the present technique encompasses the employment of inner and outer slit collimators that are not generally cylindrically shaped. By way of example, the inner and outer collimators may each be or include a flat panel having one or more slits therein to define one or more apertures.

The inner slit collimator 40 includes a plurality of inner slits 44*a*-44*e* therein. In the illustrated embodiment, these inner slits 44*a*-44*e* extend in a direction around the longitudinal axis 46 of the collimator assembly 12. In addition, the inner slit collimator 40 includes a plurality of sections spaced along the longitudinal axis 46 such that spaces between the sections define the inner slits 44*a*-44*e*. By way of example, the spaced sections may include a plurality of cylindrical sections 48*a*-48*f* spaced along the longitudinal axis 12 of the collimator assembly 12 so as to define the inner slits 44*a*-44*e*. In the illustrated embodiments, the cylindrical sections 48*a*-48*f* are coupled by rods 50 that extend in a direction parallel to the longitudinal axis 46. In exemplary embodiments, the rods 50 may be coupled to exterior surfaces of each of the cylindrical sections 48*a*-48*f* of the collimator assembly 12. For further support, each end of the rods 50 may be coupled to a coupling mechanism, such as bands 52. By way of example, each of bands 52 may be coupled to the cylindrical sections 48*a*-48*f* located at each end of the collimator assembly 12, such as section 48*a* and 48*f*, respectively. While the cylindrical sections 48*a*-48*f* of the inner slit collimator 40 are illustrated as separate sections, the present technique encompasses the use of a unitary inner slit collimator. That is, the inner slit collimator 40 may be fabricated as a solid piece having one or more slits therein. The inner slit collimator 40 may also be constructed as a unitary piece in which the slits are filled by a material that provides mechanical support but that also allows most gamma rays to pass through the slit without interaction. Suitable materials are not available at the present time.

The outer slit collimator 42 includes a plurality of outer slits 54a-54e therein. In the illustrated embodiment, the outer slits 54-54e extend in a direction generally parallel to the longitudinal axis 46 of the collimator assembly 12. In addition, the outer slit collimator 42 includes a plurality of sections spaced around the longitudinal axis 46 of the collimator assembly 12 such that spaces between the sections define the outer slits 54a-54e. By way of example, the spaced sections may be or include a plurality of panels 56a-56e spaced along the longitudinal axis 12 of the collimator assembly 12 so as to define the outer slits 54a-54e. For support, the panels 56a-56e may be coupled by a coupling mechanism, such as bands 58 illustrated in FIG. 2. By way of example, each of the bands 52 may be coupled to each of the panels 56a-56e at the respective ends of the collimator assembly 12. While the panels 56a-56e are illustrated in FIG. 2 as curved sections, the present technique encompasses the use of sections that are not curved. In addition, while the panels 56a-56e are illustrated as separate sections, the present technique encompasses the use of a unitary outer slit collimator. That is, the outer slit collimator 42 may be fabricated as a solid piece having one or more slits therein. The outer slit collimator 42 may also be constructed as a unitary piece in which the slits are filled by a material that provides mechanical support but that also allows most gamma rays to pass through the slit without interaction. Suitable materials are not available at the present time.

Those of ordinary skill in the art will appreciate that additional lines of response may be acquired by rotating one or both of the inner and/or outer slit collimators 40 and 42. If sufficient apertures (such as aperture 60) are provided by the design and construction of the collimator assembly 12, no rotation may be required to produce a SPECT image of sufficient quality. Also, if the slits are orthogonal to the longitudinal axis of the system 46, then no rotation may be required. This is the case, for example, for the inner slit collimator 40 in FIG. 2 or for the outer slit collimator 42 described below with respect to FIG. 5. Further, the inner and outer slit collimators may be mechanically coupled or placed in contact with each other, so as to rotate together, or they may be decoupled, so as to rotate separately as desired to adjust the positions of the apertures (such as aperture 60).

Figure 3:
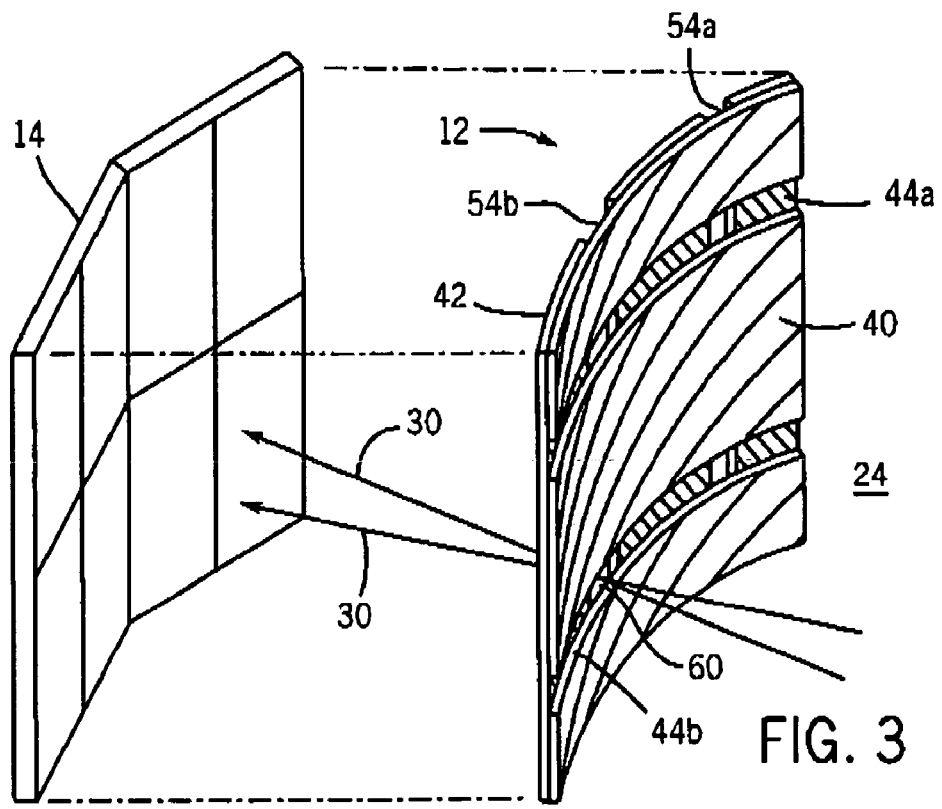
FIG. 3 is an illustration of a portion of an exemplary detector array and a portion of an exemplary collimator assembly in accordance with embodiments of the present technique.
Figure 4:
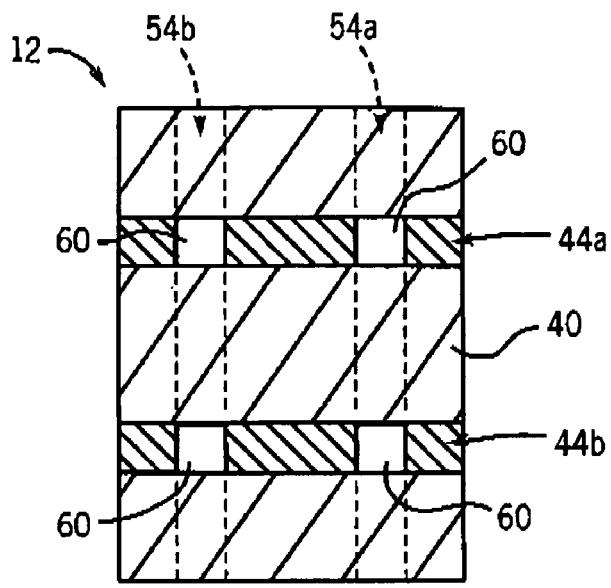
FIG. 4 is an illustration of a portion of an exemplary collimator assembly in accordance with embodiments of the present technique.

Referring now to FIGS. 3 and 4, a portion of the detector assembly 14 and a portion of the collimator assembly 12 are illustrated. As previously mentioned, the collimator assembly 12 should be configured such that the inner slits 44a-44e in the inner slit collimator 40 and the outer slits 54a-54e in the outer slit collimator 42 define one or more apertures (such as aperture 60). Gamma rays 30 that do not pass through the one or more apertures should be absorbed by the collimator assembly 12. In the illustrated embodiment, aperture 60 is defined by the intersection of inner slit 44a in the inner slit collimator 40 and outer slit 54a in the outer slit collimator 42. Aperture 60 allows gamma rays 30 emanating from the field of view 24 to pass through the collimator assembly 12 to impact the detector array 14.

In the illustrated embodiment, the inner slit 44a is generally orthogonal to the outer slit 54a (e.g., the angle of the intersection between the inner slit 44a and the outer slit 54a is approximately 90°). Because the slits are arranged in the orthogonal configuration, the aperture 60 defined by the collimator assembly 12 forms a four-sided hole through the collimator assembly 12. As illustrated, the inner slit 42a and the outer slit 54a have the same width so that the aperture 60 defined by the slits has a generally square shape. Exemplary embodiments of the present technique also may be provided with the inner slit 44a and the outer slit 54a having different widths so that the aperture 60 defined by the slits would have a generally rectangular shape. As will be discussed further with respect to FIG. 7, exemplary embodiments of the present technique also may be provided with the inner slit 44a generally oblique to the outer slit 54a (e.g., the angle of the intersection between the inner slit 44a and the outer slit 54a is different from 90°), so that the aperture 60 defined by the slits would have a generally rhombus or parallelogram shape.

Those of ordinary skill in the art will appreciate that the resolution of the SPECT system 10 is based in part on the width of the inner slits 44a-44e and the outer slits 54a-54e. In general, the inner slits 44a-44e and the outer slits 54a-54e may have the same or different widths. By way of example, the inner slits 44a-44e and the outer slits 54a-54e may have two or more different widths. In exemplary embodiments, each of the inner slits 44a-44e and the outer slits 54a-54e may have a width in the range of from about 0.1 mm to about 10 mm, typically in the range of from about 1 mm to about 5 mm. Those of ordinary skill in the art will appreciate that the choice of slit widths depends upon the system geometry (e.g., detector array 14 location and subject field of view 24) and intended imaging applications.

In addition, the inner slit collimator 40 and the outer slit collimator 42 should individually, or in combination, have a combined thickness sufficient to absorb any gamma rays that do not pass through the apertures (such as aperture 60) defined by the collimator assembly 12. By way of example, the combined thickness of the collimators may be in the range of from about 10 mm to about 30 mm. Those of ordinary skill in the art will appreciate that the required thickness to absorb gamma rays depends upon the energy of the gamma rays and the material properties of the collimator assembly. Further, the thickness of the inner and outer slit collimators 40 and 42 must each provide adequate mechanical strength to support the weight of the collimators and to allow mechanical rotation without unpredictable shape distortion.

Furthermore, those of ordinary skill in the art will appreciate that the efficiency of gamma ray detection is based on the number of apertures by the collimator assembly 12. By way of example, a collimator assembly 12 configured to define a large number of apertures (such as aperture 60) would typically require less or no rotation of the collimator assembly 12 to obtain a sufficient number of angular projections for image reconstruction. Accordingly, the number of inner slits 44a-44e and outer slits 54a-54e may be adjusted to provide the desired number of apertures, i.e., to provide the desired imaging resolution for a desired imaging time. Those of ordinary skill in the art will appreciate that the number and spacing of the apertures should be chosen with consideration of the efficient utilization of the detector assembly 14 and the performance of the image reconstruction and processing module 18. For example, limited overlap of gamma ray lines of response impacting on the detector assembly 14 may be acceptable.

While the preceding discussion of FIGS. 2-4 has described the inner slit collimator 40 as having inner slits 44a-44e extending around the longitudinal axis 46 of the collimator assembly 12 and the outer slit collimator 42 as having outer slits 54a-54e extending in a direction parallel to the longitudinal axis 46, one of ordinary skill in the art will recognize that the present technique may be implemented with collimator assemblies having inner and outer slit collimators having alternative slit configurations. In addition, those of ordinary skill in the art will also appreciate that the space between the slits in the inner and outer slit collimators 54 and 56 may or may not be constant throughout the collimator assembly 12.

Figure 5:
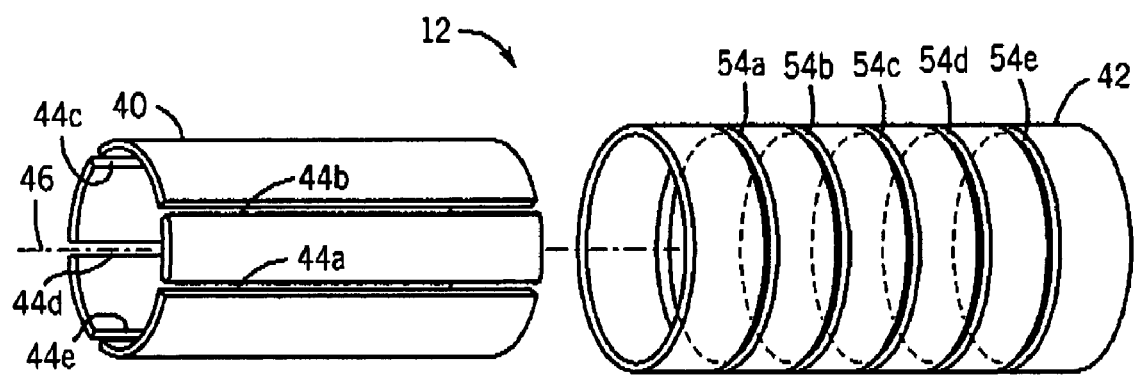
FIG. 5 is an illustration of an alternative arrangement of an exemplary collimator assembly comprising an inner slit collimator and an outer slit collimator, in accordance with embodiments of the present technique.

By way of example, FIG. 5 illustrates a collimator assembly 12 that has an inner slit collimator 40 and an outer slit collimator 42 having an alternative slit configuration. As illustrated in FIG. 5, the inner slits 44a-44e in the inner slit collimator 40 may extend in a direction generally parallel to the longitudinal axis 46 of the collimator assembly 12 while the outer slits 54a-54e in the outer slit collimator 40 extend in a direction generally orthogonal to the longitudinal axis 46 of the collimator assembly 12. As described above, the collimator assembly 12 illustrated in FIG. 5 is configured such that inner slits 44a-44e and the outer slits 54a-54e define one or more apertures through the collimator assembly 12.

Figure 6:
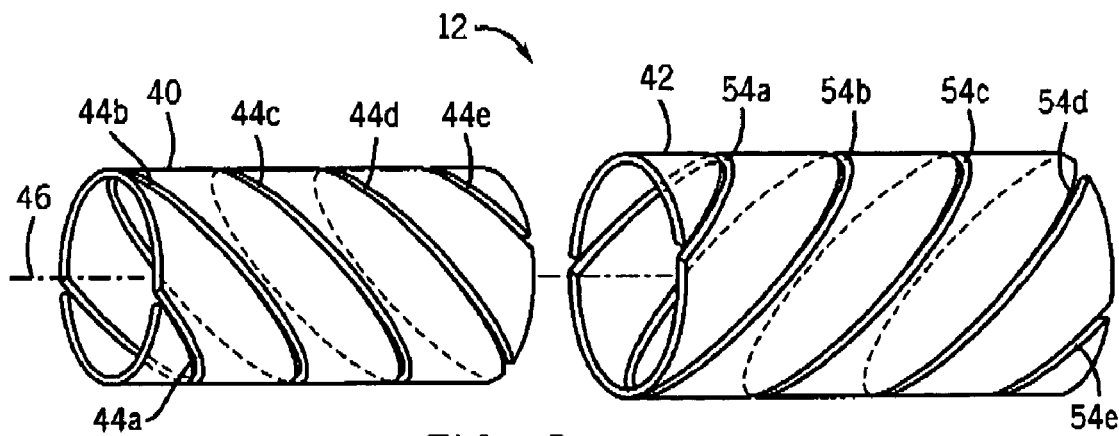
FIG. 6 is an illustration of another alternative arrangement of an exemplary collimator assembly comprising an inner slit collimator and an outer slit collimator, in accordance with embodiments of the present technique.

FIG. 6 illustrates a collimator assembly 12 that includes an inner slit collimator 40 and an outer slit collimator 42 having another alternative slit configuration. In the illustrated embodiment, the inner slits 44a-44e in the inner slit collimator 40 may extend in a direction generally diagonal to the longitudinal axis 46 of the collimator assembly 12. In the illustrated embodiment, the outer slits 54a-54e are generally orthogonal to the inner slits 54a-54e. As described above, the collimator assembly 12 illustrated in FIG. 6 is configured such that inner slits 44a-44e and the outer slits 54a-54e define one or apertures through the collimator assembly 12. Those of ordinary skill in the art will appreciate that the inner and outer slit collimators 40 and 42 may be embodied in other configurations (e.g., spirals, etc.).

Figure 7:
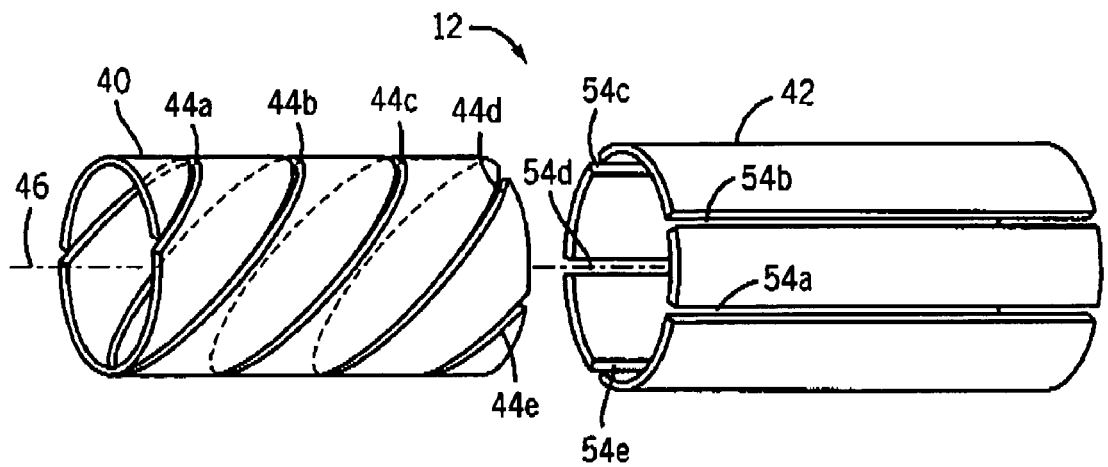
FIG. 7 is an illustration of yet another alternative arrangement of an exemplary collimator assembly comprising an inner slit collimator and an outer slit collimator, in accordance with embodiments of the present technique.

FIG. 7 illustrates a collimator assembly 12 that includes an inner slit collimator 40 and an outer slit collimator 42 having yet another alternative slit configuration. In the illustrated embodiment, the inner slits 44a-44e may be generally oblique to the outer slits 54a-54e (e.g., the angle of the intersection between the inner slits 44a-44e and the outer slits 54a-54e is different from 90°). In the illustrated embodiment, the inner slits 44a-44e in the inner slit collimator 40 may extend in a direction diagonal to the longitudinal axis 46 of the collimator assembly 12, while the outer slits 54a-54e in the outer slit collimator 40 extend in a direction generally parallel to the longitudinal axis 46 of the collimator assembly 12. As described above, the collimator assembly 12 illustrated in FIG. 7 is configured such that inner slits 44a-44e and the outer slits 54a-54e define one or more apertures through the collimator assembly 12.

Figure 8:
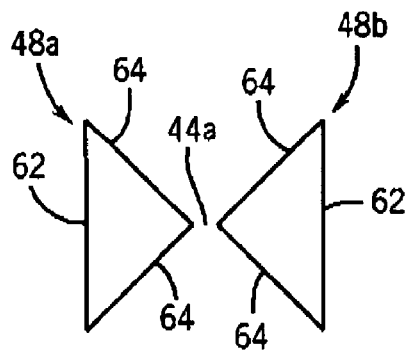
FIG. 8 is an illustration of an arrangement of one slit through an exemplary slit collimator in accordance with embodiments of the present technique.
Figure 9:
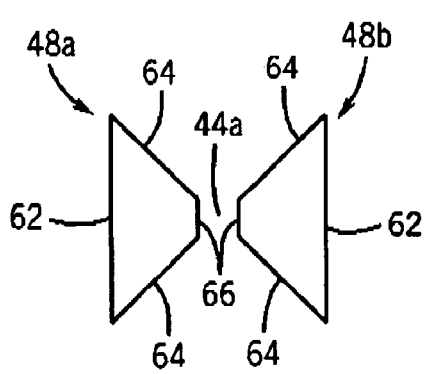
FIG. 9 is an illustration of an alternative arrangement of one slit through an exemplary slit collimator in accordance with embodiments of the present technique.
Figure 10:
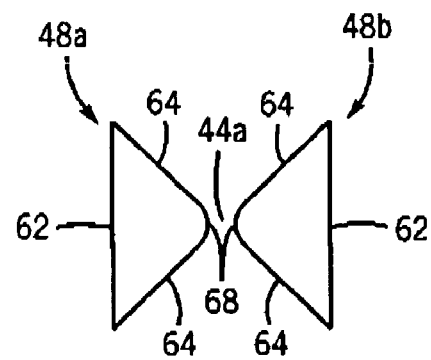
FIG. 10 is an illustration of another alternative arrangement of one slit through an exemplary slit collimator in accordance with embodiments of the present technique.

Referring now to FIGS. 8-10, a portion of the inner slit collimator 40 that defines inner slit 44a is depicted as having different slit-edge configurations. Those of ordinary skill in the art will appreciate that varying the slit-edge configuration will generally impact the resolution, sensitivity, and field of view of the SPECT system 10. In exemplary embodiments, the inner slit collimator 40 and the outer slit collimator 42 may be configured as having slits edges that are sharp (e.g., knife-edge) or blunted (e.g., keel-edge or round edge). Other slit edge configurations may also be suitable. Those of ordinary skill in the art will appreciate that the slit edge configuration may be selected based on, inter alia, the desired resolution, sensitivity, and field of view, including consideration of the performance of the image reconstruction and processing module 18. Further, the slit edges may be constructed from the same or different material as that used for the photon-absorbing collimator sections 48 or 56.

FIG. 8 illustrates a portion of the inner slit collimator 40 having a knife-edge configuration in accordance with an embodiment of the present technique. As illustrated, inner slit 44a is defined by the tips 62 of the cylindrical sections 48a and 48b of the inner slit collimator 40. In the illustrated embodiment, the tips 62 comprise angled segments 64 that define inner slit 44a as having a knife-edge.

FIG. 9 illustrates a portion of the inner slit collimator 40 having a keel-edge configuration in accordance with an embodiment of the present technique. As illustrated, inner slit 44a is defined by the tips 62 of the cylindrical sections 48a and 48b of the inner slit collimator 40. In the illustrated embodiment, the tips 62 comprise angled segments 64 and blunt ends 66 that define inner slit 44a as having a keel-edge.

FIG. 10 illustrates a portion of the inner slit collimator 40 having a round-edge configuration in accordance with an embodiment of the present technique. As illustrated, inner slit 44a is defined by the tips 62 of the cylindrical sections 48a and 48b of the inner slit collimator 40. In the illustrated embodiment, the tips 62 comprise angled segments 64 and round ends 68 that define inner slit 44a as having a round-edge.

Moreover, those of ordinary skill in the art will recognize that the SPECT system 10 may require calibration. Calibration of the SPECT system 10 may require, for example, use of a radioactive source without the subject 28 present in the field of view 24. In general, slit collimators typically require line sources while pinhole collimators require point sources. However, while the inner slit collimator 40 and the outer slit collimator 42 are slit collimators, they are arranged to form a collimator assembly 12 having multiple pinhole apertures therein, rather than slits. As such, the SPECT system 10 comprising the inner slit collimator 40 and the outer slit collimator 42 may be calibrated with a point source.

Figure 11:
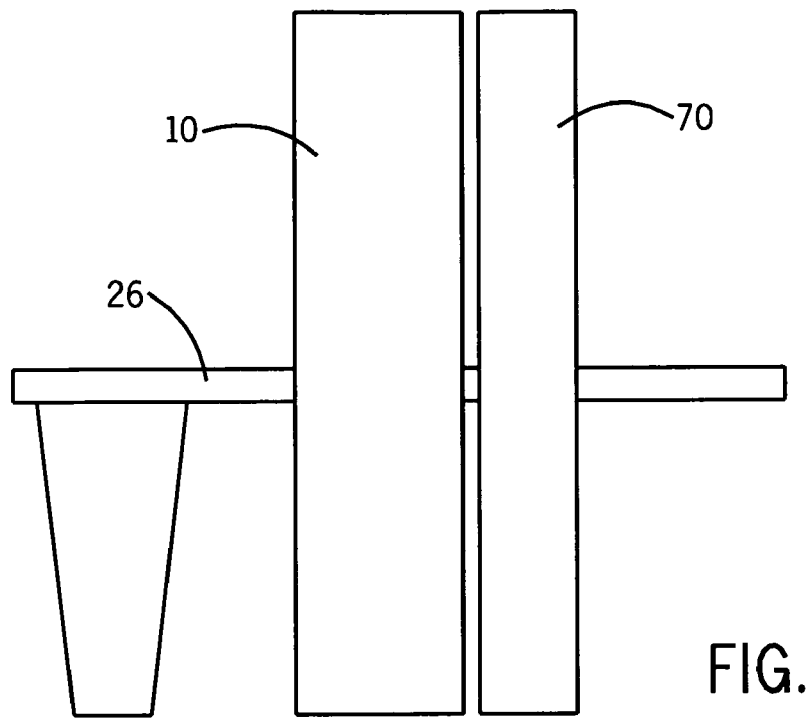
FIG. 11 is an illustration of an exemplary combined SPECT and computed tomography (CT) system in accordance with embodiments of the present technique.
Figure 12:
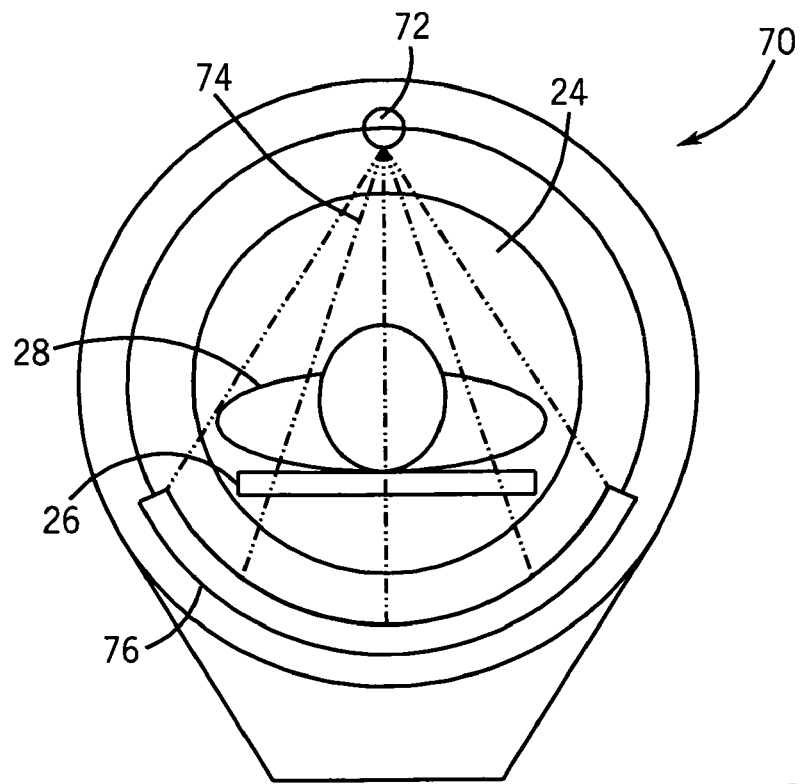
FIG. 12 is an illustration of an exemplary CT system that can be combined with a SPECT system, in accordance with embodiments of the present technique.

While specific reference in the present discussion is made to a SPECT system, it should be appreciated that the present technique is not intended to be limited to this or any other specific type of imaging system or modality. Rather, exemplary embodiments of the present technique may be used in conjunction with other imaging modalities, e.g., coded-aperture astronomy. In addition, SPECT system 10 may be combined with a second imaging system, such as a CT system or a magnetic resonance imaging (MRI) system. By way of example, the SPECT system 10 may be combined in the same gantry with a CT system. As illustrated in FIG. 11, a SPECT/CT imaging system includes SPECT system 10 and CT system 70. By way of example, the SPECT system 10 and the CT system 70 are shown as separate modules, aligned along a common longitudinal axis, and sharing a single subject support 26. As illustrated by FIG. 12, CT system 70 includes a source 72 of x-ray radiation configured to emit a stream of radiation 74 in the direction of the field of view 24 and an X-ray detector array 76 configured to generate one or more signals in response to the stream of radiation. Those of ordinary skill in the art will appreciate that in the third-generation CT configuration illustrated in FIG. 12, the source 72 and the X-ray detector array 76 generally rotate in synchrony around the field of view while acquiring a plurality of lines of response passing through the subject, so that an x-ray tomographic attenuation image may be reconstructed. Other CT configurations may be employed, including the shared use of at least a portion of the SPECT detector array 14 as the X-ray detector array 76. Further, the SPECT and CT images may be acquired sequentially, in any order, by repositioning the subject, or concurrently by sharing the detector array. The images generated with the CT system may then be used to generate gamma ray attenuation maps, for example, to calculate attenuation and/or scatter correction during the SPECT image reconstruction. In addition, the CT anatomical images may be combined with the SPECT functional images.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A collimator assembly comprising:
an outer slit collimator having one or more slits therein; and
an inner slit collimator having one or more slits therein;
wherein the outer slit collimator and the inner slit collimator are each generally cylindrical.

2. The collimator assembly of claim 1, wherein the collimator is generally cylindrically shaped.

3. The collimator assembly of claim 1, wherein the slits in the outer slit collimator are generally orthogonal to the slits in the inner slit collimator.

4. The collimator assembly of claim 1, wherein the slits in the outer slit collimator are generally oblique to the slits in the inner slit collimator.

5. The collimator assembly of claim 1, wherein the collimator assembly comprises a longitudinal axis, wherein the slits in the inner slit collimator extend in a direction generally parallel to the longitudinal axis of the collimator assembly.

6. The collimator assembly of claim 1, wherein the collimator assembly comprises a longitudinal axis, wherein the slits in the inner slit collimator extend in a direction generally orthogonal to the longitudinal axis of the collimator assembly.

7. The collimator assembly of claim 1, wherein the collimator assembly comprises a longitudinal axis, wherein the slits in the inner slit collimator extend in a direction generally diagonal to the longitudinal axis of the collimator assembly.

8. The collimator assembly of claim 1, wherein the inner slit collimator and the outer slit collimator are affanged such that the slits in the inner slit collimator and the slits in the outer slit collimator align to define a plurality of apertures for gamma rays emanating from a field of view.

9. The collimator assembly of claim 1, wherein the slit edges in the inner slit collimator and the slit edges in the outer slit collimator are sharp or blunted.

10. The collimator assembly of claim 1, wherein the slits in the inner slit collimator and the slits in the outer slit collimator have a width in the range of from about 0.1 mm to about 10 mm.

11. The collimator assembly of claim 1, wherein the slits in the inner slit collimator and/or the outer slit collimator include slits with two or more different widths.

12. An imaging system, comprising:
a collimator assembly comprising an outer slit collimator having one or more slits therein, and an inner slit collimator having one or more slits therein; and wherein the outer slit collimator and the inner slit collimator are each generally cylindrical;
a detector array configured to detect gamma rays emanating from a field of view that pass through one or more apertures defined by the collimator assembly and generate one or more signals in response to the detected gamma rays.

13. The system of claim 12, wherein the slits in the outer slit collimator are generally orthogonal to the slits in the inner slit collimator.

14. The system of claim 12, wherein the slits in the outer slit collimator are generally oblique to the slits in the inner slit collimator.

15. The system of claim 12, wherein the collimator assembly comprises a longitudinal axis, wherein the slits in the inner slit collimator extend in a direction generally parallel to the longitudinal axis of the collimator assembly.

16. The system of claim 12, wherein the collimator assembly comprises a longitudinal axis, wherein the slits in the inner slit collimator extend in a direction generally orthogonal to the longitudinal axis of the collimator assembly.

17. The system of claim 12, wherein the collimator assembly comprises a longitudinal axis, wherein the slits in the inner slit collimator extend in a direction generally diagonal to the longitudinal axis of the collimator assembly.

18. The system of claim 12, wherein the detector away comprises an away of solid-state detector elements.

19. The system of claim 12, wherein the collimator assembly is configured to rotate with respect to the detector array.

20. The system of claim 12, wherein both the detector array and the collimator assembly are both configured to rotate.

21. The system of claim 12, comprising:
a module configured to receive the one or more signals and to process the one or more signals to generate one or more images; and
an image display workstation configured to display the one or more images.

22. The system of claim 12, comprising a source of x-ray radiation configured to emit radiation in the direction of the field of view.

23. The system of claim 12, wherein the collimator extends from 1800 to 3600 around the field of view.

24. A method of imaging a volume, comprising: positioning at least a portion of a subject in a field of view of a single photon emission computed tomography system;
collimating gamma rays emitted from the portion of the subject using a collimator assembly comprising an outer slit collimator and an inner slit collimator that are each generally cylindrical, wherein gamma rays aligned with apertures formed by overlapping slits of the outer slit collimator and the inner slit collimator pass through the collimator assembly, and wherein the collimator assembly absorbs gamma rays not aligned with the apertures;
detecting the gamma rays that pass through the collimator assembly; and generating one or more signals in response to the detected gamma rays.

25. The method of claim 24 comprising processing the one or more signals to generate one or more images and displaying the one or more images on an operator workstation.

26. The method of claim 24 comprising rotating the collimator assembly with respect to a detector array.

27. The method of claim 24 comprising rotating the collimator assembly and rotating the detector array.

28. The method of claim 24 comprising acquiring anatomical images and single photon emission computed tomography images.

* * * * *

UNITED STATES PATENT AND TRADEMARK OFFICE
CERTIFICATE OF CORRECTION

PATENT NO. : 7,470,907 B2  Page 1 of 1
APPLICATION NO. : 11/639786
DATED : December 30, 2008
INVENTOR(S) : Hugg et al.

It is certified that error appears in the above-identified patent and that said Letters Patent is hereby corrected as shown below:

In Column 11, Line 36, in Claim 8, delete "affanged" and insert -- arranged --, therefor.

In Column 12, Line 19, in Claim 18, delete "away" and insert -- array --, therefor.

In Column 12, Line 20, in Claim 18, delete "away" and insert -- array --, therefor.

In Column 12, Line 35, in Claim 23, delete "1800 to 3600" and insert -- 180° to 360° --, therefor.

Signed and Sealed this

Thirty-first Day of August, 2010

David J. Kappos
*Director of the United States Patent and Trademark Office*